United States Patent [19]
Cataneo et al.

[11] Patent Number: 5,866,104
[45] Date of Patent: Feb. 2, 1999

[54] NAIL POLISH REMOVER

[76] Inventors: Robert Cataneo, 9B Evergreen Cir., Savoy, Ill. 61874; Ralph Cataneo, 1169 E. 21st St., Brooklyn, N.Y. 11210

[21] Appl. No.: 945,540

[22] Filed: Sep. 16, 1992

Related U.S. Application Data

[63] Continuation-in-part of Ser. No. 528,348, May 22, 1990, abandoned, which is a continuation of Ser. No. 226,953, Aug. 1, 1988, abandoned, and a continuation-in-part of Ser. No. 379,182, Jul. 13, 1989, abandoned, which is a continuation-in-part of Ser. No. 226,953, Aug. 1, 1988, abandoned.

[51] Int. Cl.$^6$ .................................................. A61K 7/047
[52] U.S. Cl. .............................. 424/61; 424/401; 510/118
[58] Field of Search ............................... 424/401, 61, 47; 510/118

[56] References Cited

U.S. PATENT DOCUMENTS

| | | | |
|---|---|---|---|
| 3,124,825 | 3/1964 | Iovenko | 15/104.93 |
| 3,697,643 | 10/1972 | Shepherd et al. | 424/70.7 |
| 3,832,235 | 8/1974 | Cooper et al. | 132/31 |
| 3,864,294 | 2/1975 | Busch, Jr. | 106/271 |
| 4,098,744 | 7/1978 | Allen et al. | 523/416 |
| 4,119,609 | 10/1978 | Allen et al. | 525/510 |
| 4,122,234 | 10/1978 | Lohoff | 428/413 |
| 4,124,554 | 11/1978 | Fry | 523/412 |
| 4,158,053 | 6/1979 | Greene et al. | 424/61 |
| 4,240,450 | 12/1980 | Grollier et al. | 132/209 |
| 4,304,563 | 12/1981 | Grollier et al. | 8/127.51 |
| 4,365,039 | 12/1982 | Blegen | 524/773 |
| 4,409,203 | 10/1983 | Gordon et al. | 424/61 |
| 4,419,326 | 12/1983 | Santini | 422/4 |
| 4,445,521 | 5/1984 | Grollier et al. | 132/202 |
| 4,530,726 | 7/1985 | Montiel | 134/6 |
| 4,747,419 | 5/1988 | Flynn et al. | 132/73 |
| 4,762,703 | 8/1988 | Abrutyn | 424/61 |
| 4,781,916 | 11/1988 | Papaphilippou | 424/61 |
| 4,798,720 | 1/1989 | Holder | 424/61 |
| 4,822,423 | 4/1989 | Soyama et al. | 424/61 |
| 4,842,849 | 6/1989 | Grollier et al. | 424/70.13 |
| 4,948,697 | 8/1990 | Durham | 430/165 |
| 5,645,823 | 7/1997 | Thrall et al. | 424/61 |
| 5,667,768 | 9/1997 | Ramin | 424/61 |
| 5,681,550 | 10/1997 | Rubino | 424/61 |

*Primary Examiner*—Robert H. Harrison
*Attorney, Agent, or Firm*—Philip L. Bateman

[57] ABSTRACT

A nail polish remover comprises about 25 to 95% glycol ether ester and about 5 to 75% glycol ether. The remover preferably comprises about 5 to 40% water. The remover is highly effective and yet is gentle to the nails and skin and relatively hazard-free. The remover is free of acetone and ethyl acetate, the two most widely used and hazardous solvents in current commercial nail polish removers.

14 Claims, No Drawings

NAIL POLISH REMOVER

CROSS-REFERENCE TO RELATED APPLICATIONS

This application is a continuation-in-part of Ser. No. 07/528,348, May 22, 1990, now abandoned; which is a continuation of Ser. No. 07/226,953, Aug. 1, 1988, now abandoned; and is also a continuation-in-part of Ser. No. 07/379,182, Jul. 13, 1989, now abandoned; which is a continuation-in-part of Ser. No. 07/226,953, Aug. 1, 1988, now abandoned.

FIELD OF THE INVENTION

This invention relates to compositions for removing nail polish from human nails. More particularly, this invention relates to nail polish removers containing a glycol ether ester and a glycol ether as their major ingredients, instead of acetone or ethyl acetate, the two most widely used and hazardous components in present commercial nail polish removers.

BACKGROUND OF THE INVENTION

For thousands of years it has been customary for women to coat their nails with colored polish. Current commercial nail polishes are made of colors and acrylic resins dissolved or suspended in a solvent base. Nail polish removers are used to remove the polish from the nails. In the United States, about four million gallons of nail polish remover are sold annually, or about five fluid ounces per each woman of age 13 and above.

Present commercial nail polish removers generally contain either acetone or ethyl acetate. Each of these solvents is inexpensive and highly effective at removing nail polish. Unfortunately, each suffers from a large number of serious health problems: Each solvent is highly flammable, can cause dermatitis or other skin problems because it removes fat from the skin, can cause lung damage if inhaled, exhibits a moderate level of toxicity if ingested, and contains small amounts of known carcinogens such as benzene, formaldehyde, and acetaldehyde.

Because of these serious health problems, the use of acetone and ethyl acetate in nail polish removers will soon diminish or end altogether. The State of California has set a maximum level of 85% for volatile organic compounds (VOCs) in nail polish removers sold after Jan. 1, 1994 and a maximum level of 75% after Jan. 1, 1996. A VOC is defined as an organic compound having a vapor pressure at 20° C. of greater than 0.1 mm Hg. Both acetone and ethyl acetate are, of course, within this definition. Other states, as well as the federal government, are expected to impose similar requirements in the near future. Accordingly, it is essential that an effective nail polish remover be provided which reduces or eliminates the health hazards associated with acetone and ethyl acetate and which meets the upcoming VOC limitations.

Compositions for treating keratinic materials such as human skin, hair, and nails are disclosed in a series of patents issued to Grollier et al.: U.S. Pat. No. 4,240,450, issued Dec. 23, 1980; U.S. Pat. No. 4,304,563, issued Dec. 8, 1981; U.S. Pat. No. 4,445,521, issued May 1, 1984; and U.S. Pat. No. 4,842,849, issued Jun. 27, 1989. Glycol ether esters and glycol ethers are mentioned as optional, cosmetically acceptable solvents in these compositions. Papaphilippou, U.S. Pat. No. 4,781,916, issued Nov. 1, 1988, discloses a nail polish remover containing a diester of a diol or dioic acid. Optional ingredients include moisturizers such as the monoalkyl ethers of ethylene and propylene glycol.

SUMMARY OF THE INVENTION

The general object of this invention is to provide an improved nail polish remover. A more particular object is to provide a nail polish remover containing neither acetone nor ethyl acetate. Another more particular object is to provide a nail polish remover which is effective in removing polish, is relatively hazard-free, and meets the upcoming VOC limitations.

We have invented an improved nail polish remover. The nail polish remover comprises: (a) about 25 to 95% glycol ether ester; and (b) about 5 to 75% glycol ether. The nail polish remover preferably additionally comprises about 5 to 40% water.

This nail polish remover is a stable, homogeneous solution which is highly effective at removing nail polish. It removes the polish gently and completely without redepositing dissolved polish back onto the nails, leaving the nails primed for a fresh coat of polish. In addition, this nail polish remover exhibits many advantages over acetone- and ethyl acetate-based removers. First, this remover is much less flammable. Second, it removes much less fat from the skin so it has less tendency to cause dermatitis or other skin problems. Third, it is relatively non-toxic if inhaled or ingested. Fourth, it contains no known carcinogens. Fifth, it is suitable for use on artificial nails. Sixth, this remover has a relatively low vapor pressure, allowing plastic containers to be used with relatively thin walls. Seventh, preferred embodiments contain sufficient amounts of water and other components not defined as VOCs so that upcoming VOC limitations are met.

DETAILED DESCRIPTION OF THE INVENTION

The nail polish remover of this invention comprises a glycol ether ester and a glycol ether. It preferably also comprises water. Other preferred components include co-solvents and aesthetic agents. Each of these components, and the use of the remover to remove polish from the nails, is discussed in turn.

A glycol ether ester is a compound which can be considered a derivative of ethylene glycol, $CH_2OHCH_2OH$; propylene glycol, $CH_3CHOHCH_2OH$; diethylene glycol, $(CH_2OHCH_2)_2O$; or dipropylene glycol, $(CH_3CHOHCH_2)_2O$. Glycol ether esters include mono glycol ether esters such as ethylene glycol monomethyl ether acetate (sold commercially under the trademark Methyl Cellosolve Acetate), ethylene glycol monoethyl ether acetate (Cellosolve Acetate), ethylene glycol monobutyl ether acetate (Butyl Cellosolve Acetate), ethylene glycol monoethyl ether propionate (UCAR Ester EEP), and propylene glycol monomethyl ether acetate (Methyl Propasol Acetate). Glycol ether esters also include di glycol ether esters such as diethylene glycol monoethyl ether acetate (Carbitol Acetate), diethylene glycol monobutyl ether acetate (Butyl Carbitol Acetate), and dipropylene glycol monomethyl ether acetate (Arcosolv DPM Acetate). The preferred esters are propylene glycol monomethyl ether acetate, ethylene glycol monoethyl ether acetate, and ethylene glycol monobutyl ether acetate because of their effectiveness in removing nail polish and their low toxicities. The most preferred ester is propylene glycol monomethyl ether acetate.

The ester comprises about 25 to 95 volume percent of the nail polish remover. All percentages hereinafter are given on a volume basis. However, the densities of the major components are similar so the resulting weight percentages are also similar. If the ester percentage is less than about 25% or greater than about 95%, the effectiveness of nail polish removal suffers. The remover preferably comprises about 40 to 95% ester, and most preferably about 50 to 85%.

A glycol ether is also a compound which can also be considered a derivative of ethylene glycol, propylene glycol, diethylene glycol, or dipropylene glycol. Glycol ethers include mono glycol ethers and di glycol ethers. Examples of mono glycol ethers include ethylene glycol monomethyl ether (Methyl Cellosolve), ethylene glycol monoethyl ether (Cellosolve), ethylene glycol monopropyl ether (Propyl Cellosolve), ethylene glycol monobutyl ether (Butyl Cellosolve), ethylene glycol monohexyl ether (Hexyl Cellosolve), ethylene glycol monophenyl ether (Dowanol EPH), propylene glycol monomethyl ether (Methyl Propasol), propylene glycol monopropyl ether (Propyl Propasol), propylene glycol monobutyl ether (Butyl Propasol), propylene glycol t-butyl ether (Arcosolv PTB), and propylene glycol monophenyl ether (Dowanol PPH). Representative di glycol ethers include diethylene glycol monomethyl ether (Methyl Carbitol), diethylene glycol monoethyl ether (Carbitol), diethylene glycol monopropyl ether (Propyl Carbitol), diethylene glycol monobutyl ether (Butyl Carbitol), diethylene glycol monohexyl ether (Hexyl Carbitol), dipropylene glycol monomethyl ether (Arcosolv DPM), and dipropylene glycol n-butyl ether (Dowanol DPNB).

The preferred ethers are propylene glycol monomethyl ether, ethylene glycol monopropyl ether, and ethylene glycol monobutyl ether. These ethers function well in removing nail polish and are relatively non-toxic. The most preferred ether is propylene glycol monomethyl ether. The combination of this ether with its simplest ester analog, propylene glycol monomethyl ether acetate, produces a highly effective remover. The ether comprises about 5 to 75%, preferably about 5 to 40%, and most preferably about 5 to 25% of the remover.

The nail polish remover of this invention preferably comprises about 5 to 40% water. Water is a preferred component for a number of reasons. Most importantly, the presence of water synergistically enhances the effectiveness of the remover. While not wishing to be bound by theory, it is believed that the highly polar water molecules enhance the solvating properties of the ester-ether combination. In turn, it is believed that the ester-ether combination dramatically reduces the surface tension of the water, thereby increasing the substrate-film-wetting ability of the remover. The improved wetting provides better film penetration of the polish and, therefore, faster dissolving of the hardened polish. It is also believed that the water plays a major role in causing the dissolved polish to be retained within the applicator rather than being redeposited onto the nails. Another important reason water is a preferred component is because it enables the remover to meet the upcoming limitations on VOCs. While the ester and ether are VOCs, water is, of course, not a VOC. Accordingly, the presence of 15% water enables the remover to meet an 85% VOC limitation, even without any other non-VOC components being present. A final reason water is a preferred component is that it reduces the cost of the remover. The remover preferably comprises about 5 to 30% water, and most preferably about 10 to 20% water.

A second, preferred component of the nail polish remover is a co-solvent. The presence of up to about 15% co-solvent increases the solvating ability of the remover. The co-solvent also acts as a conditioning agent for the nails and skin, thereby preventing the whitish film often associated with acetone- and ethyl acetate-based removers. The co-solvent is preferably present in an amount up to about 10%. Preferred co-solvents are 2-methyl-1,3-propanediol, propylene glycol, and polyoxypropylene-polyoxyethylene block copolymers. Because of their low vapor pressures, none of these co-solvents is defined as a VOC. The preferred co-solvent is 2-methyl-1,3-propanediol.

Other optional ingredients in the nail polish remover of this invention include a variety of components whose primary function is to improve the aesthetics of the remover rather than to improve its effectiveness in polish removal. Such aesthetic agents include fragrances (also known as masking agents), colorings, emollients, and the like. The aesthetic agents generally comprise less than about 5% of the composition, and preferably less than about 2%.

The nail polish remover of this invention is generally packaged and used in a conventional manner. However, this remover has a vapor pressure considerably less than acetone- or ethyl acetate-based removers and, therefore, offers additional options. For example, current commercial removers are usually sold in liquid form and are poured onto cotton balls or absorbent pads which are then wiped against the polished nails. Such liquid containers are typically made of high density polyethylene, have a wall thickness of about 0.08 inches, and have tightly-sealing caps in order to limit the amount of evaporation. With the less-volatile remover of this invention, wall thicknesses of only about 0.04 inches are adequate, resulting in significant weight and cost savings, and in a reduced contribution to the solid waste stream. The relatively low volatility of the remover also makes it feasible to package the remover in the form of pre-wetted absorbent pads or sheets. Other suitable application devices and methods are shown in Iovenko, U.S. Pat. No. 3,124,825, issued Mar. 17, 1964; and Montiel, U.S. Pat. No. 4,530,726, issued Jul. 23, 1985; each of which is incorporated by reference.

The following examples are illustrative only.

EXAMPLE 1

This example illustrates the effectiveness of various compositions in removing nail polish. A smooth, white, circular (approximately 3 inches in diameter), flat surface of polypropylene was coated with a layer of Revlon nail polish, a commercial product of Revlon, Inc., New York, N.Y., or a similar commercial product. The main ingredients of the Revlon nail polish are, in descending order, toluene, butyl acetate, ethyl acetate, and nitrocellulose. After one hour, a second coat was applied. The polish was then cured under room conditions for three days.

Three milliliters of the composition to be evaluated were then poured into a triple-size cosmetic cotton ball. The cotton ball was then rubbed against the polish spot in a circular motion applying uniform pressure. The number of rubs necessary to remove the spot was recorded.

Forty-five runs with different compositions were conducted using this procedure. The results are shown in Table 1. Where indicated, a scented fragrance oil was used as a masking agent to improve the aesthetics of the remover. The fragrance oil was a commercial product of Florasynth, Inc.

of New York, N.Y. The following abbreviations are used in Table 1:

Esters
PGMMEA—propylene glycol monomethyl ether acetate
EGMEEA—ethylene glycol monoethyl ether acetate
EGMBEA—ethylene glycol monobutyl ether acetate
DGMBEA—diethylene glycol monobutyl ether acetate
Ethers
PGMME—propylene glycol monomethyl ether
EGMPE—ethylene glycol monopropyl ether
EGMBE—ethylene glycol monobutyl ether
DGMEE—diethylene glycol monoethyl ether
DGMPE—diethylene glycol monopropyl ether
DGMBE—diethylene glycol monobutyl ether
Co-Solvents
MP—2-methyl-1,3-propanediol
PG—propylene glycol
PPBC—polyoxypropylene-polyoxyethylene block copolymer

EXAMPLE 2

This example illustrates the sensory impressions of human models to various nail polish remover compositions. Fifty-six women of varied ages and occupations who regularly use conventional nail polish removers containing acetone or ethyl acetate agreed to use an experimental remover exclusively for thirty days. The experimental remover consisted of 52.7% propylene glycol monomethyl ether acetate, 16.3% propylene glycol monomethyl ether, 21.0% water, 9.0% 2-methyl-1,3-propanediol, and 1.0% scented fragrance oil. The women were not told of the composition of the experimental remover. At the end of the thirty day period, the women completed a questionnaire asking them to compare the experimental remover with their conventional remover in seven categories. The results of the questionnaires are shown in Table 2. The numbers represent the percentages of women who gave the indicated response.

TABLE 1

| Run No. | Identity of Components | | | Amounts of Components (Vol. %) | | | | Mask | No. of Rubs |
|---|---|---|---|---|---|---|---|---|---|
| | Ester | Ether | Co-Solv | Ester | Ether | Water | Co-Solv | | |
| 1  | PGMMEA | PGMME | MP   | 85   | 5    | 5    | 4   | 1   | 2  |
| 2  | PGMMEA | PGMME | MP   | 75   | 5    | 10   | 9   | 1   | 2  |
| 3  | PGMMEA | PGMME | PG   | 85   | 5    | 5    | 4   | 1   | 2  |
| 4  | PGMMEA | PGMME | MP   | 65   | 10   | 15   | 9   | 1   | 3  |
| 5  | PGMMEA | PGMME | MP   | 50   | 20   | 20   | 9   | 1   | 4  |
| 6  | PGMMEA | —     | MP   | 95   | —    | —    | 4   | 1   | 4  |
| 7  | PGMMEA | PGMME | MP   | 90   | 5    | —    | 4   | 1   | 4  |
| 8  | PGMMEA | PGMME | PG   | 75   | 5    | 10   | 9   | 1   | 4  |
| 9  | PGMMEA | PGMME | PG   | 65   | 10   | 15   | 9   | 1   | 4  |
| 10 | PGMMEA | PGMME | MP   | 50   | 15   | 20   | 14  | 1   | 5  |
| 11 | PGMMEA | PGMME | PG   | 50   | 20   | 20   | 9   | 1   | 5  |
| 12 | PGMMEA | PGMME | PPBC | 60   | 16   | 20   | 3.5 | 0.5 | 5  |
| 13 | PGMMEA | PGMME | PPBC | 50   | 25   | 21   | 3.5 | 0.5 | 6  |
| 14 | PGMMEA | PGMME | MP   | 40   | 20   | 30   | 9   | 1   | 7  |
| 15 | PGMMEA | PGMME | PPBC | 55   | 16   | 25   | 3.5 | 0.5 | 7  |
| 16 | PGMMEA | PGMME | PPBC | 55   | 17   | 24   | 3.5 | 0.5 | 7  |
| 17 | PGMMEA | PGMME | PPBC | 56   | 17.3 | 24.4 | 1.8 | 0.5 | 7  |
| 18 | PGMMEA | PGMME | PPBC | 46   | 26   | 25   | 3   | —   | 8  |
| 19 | PGMMEA | PGMME | PPBC | 46   | 20   | 31   | 3   | —   | 8  |
| 20 | PGMMEA | PGMME | PPBC | 45   | 18   | 33   | 3.5 | 0.5 | 8  |
| 21 | PGMMEA | PGMME | PPBC | 41   | 25   | 31   | 3   | —   | 9  |
| 22 | PGMMEA | PGMME | PPBC | 41   | 24   | 31   | 3.5 | 0.5 | 9  |
| 23 | PGMMEA | PGMME | PPBC | 41   | 20   | 35   | 3.5 | 0.5 | 9  |
| 24 | PGMMEA | PGMME | PPBC | 37   | 28   | 31   | 3.5 | 0.5 | 10 |
| 25 | PGMMEA | PGMME | PPBC | 37   | 21   | 38   | 3.5 | 0.5 | 10 |
| 26 | PGMMEA | PGMME | PPBC | 37   | 22   | 38   | 2.5 | 0.5 | 10 |
| 27 | PGMMEA | PGMME | MP   | 10   | 55   | 30   | 4   | 1   | 10 |
| 28 | PGMMEA | PGMME | PPBC | 36   | 36   | 25   | 3   | —   | 11 |
| 29 | PGMMEA | PGMME | PPBC | 32.5 | 33   | 31.5 | 3   | —   | 11 |
| 30 | PGMMEA | PGMME | MP   | 5    | 85   | 5    | 4   | 1   | 11 |
| 31 | PGMMEA | PGMME | PPBC | 10   | 56   | 31   | 3   | —   | 12 |
| 32 | —      | PGMME | MP   | —    | 95   | —    | 4   | 1   | 12 |
| 33 | —      | EGMPE | —    | —    | 100  | —    | —   | —   | 13 |
| 34 | —      | EGMPE | PPBC | —    | 96   | —    | 4   | —   | 13 |
| 35 | —      | EGMPE | PPBC | —    | 90   | 5    | 3   | 2   | 13 |
| 36 | EGMEEA | EGMPE | PPBC | 20   | 65   | 10   | 4   | 1   | 14 |
| 37 | EGMEEA | —     | PPBC | 90   | —    | 5    | 4   | 1   | 15 |
| 38 | EGMBEA | —     | PPBC | 98   | —    | —    | 2   | —   | 16 |
| 39 | —      | EGMBE | —    | —    | 100  | —    | —   | —   | 17 |
| 40 | —      | EGMBE | PPBC | —    | 96   | —    | 4   | —   | 17 |
| 41 | DGMBEA | —     | PPBC | 98   | —    | —    | 2   | —   | 17 |
| 42 | —      | EGMBE | PPBC | —    | 90   | 5    | 4   | 1   | 18 |
| 43 | —      | DGMEE | PPBC | —    | 98   | —    | 2   | —   | 19 |
| 44 | —      | DGMPE | PPBC | —    | 98   | —    | 2   | —   | 20 |
| 45 | —      | DGMBE | PPBC | —    | 98   | —    | 2   | —   | 20 |

TABLE 2

| Category of Comparison | Exp. Remover Better (%) | Both Removers Equal (%) | Conv. Remover Better (%) |
| --- | --- | --- | --- |
| Gentleness | 92 | 8 | 0 |
| Conditioning Nails | 100 | 0 | 0 |
| Color Residue | 66 | 34 | 0 |
| Fragrance | 75 | 25 | 0 |
| Speed of Removal | 25 | 50 | 25 |
| Thoroughness of Removal | 58 | 33 | 9 |
| Overall Performance | 92 | 8 | 0 |

The results show that the experimental remover containing a glycol ether ester, a glycol ether, and water was judged equal to conventional removers in speed of polish removal and was judged superior to conventional removers in every other category. In particular, 51 of 56 women (92%) using the experimental remover judged it superior in overall performance.

We claim:

1. A nail polish remover consisting essentially of: (a) about 25 to 95% glycol ether ester; (b) about 5 to 75% glycol ether; and (c) about 5 to 40% water.

2. The nail polish remover of claim 1 wherein the ester comprises ethylene glycol monomethyl ether acetate, ethylene glycol monoethyl ether acetate, ethylene glycol monobutyl ether acetate, ethylene glycol monoethyl ether propionate, propylene glycol monomethyl ether acetate, diethylene glycol monoethyl ether acetate, diethylene glycol monobutyl ether acetate, or dipropylene glycol monomethyl ether acetate.

3. The nail polish remover of claim 2 wherein the ether comprises ethylene glycol monomethyl ether, ethylene glycol monoethyl ether, ethylene glycol monopropyl ether, ethylene glycol monobutyl ether, ethylene glycol monohexyl ether, ethylene glycol monophenyl ether, propylene glycol monomethyl ether, propylene glycol monopropyl ether, propylene glycol monobutyl ether, propylene glycol t-butyl ether, propylene glycol monophenyl ether, diethylene glycol monomethyl ether, diethylene glycol monoethyl ether, diethylene glycol monopropyl ether, diethylene glycol monobutyl ether, diethylene glycol monohexyl ether, dipropylene glycol monomethyl ether, and dipropylene glycol n-butyl ether.

4. A nail polish remover consisting essentially of: (a) about 25 to 95% glycol ether ester; (b) about 5 to 75% glycol ether; (c) about 5 to 40% water; and (d) an effective amount up to about 15% co-solvent.

5. The nail polish remover of claim 4 wherein the ester comprises about 40 to 95% of the remover.

6. The nail polish remover of claim 5 wherein the ether comprises about 5 to 40% of the remover.

7. The nail polish remover of claim 6 wherein water comprises about 5 to 30% of the remover.

8. The nail polish remover of claim 7 wherein the ester comprises propylene glycol monomethyl ether acetate, ethylene glycol monoethyl ether acetate, or ethylene glycol monobutyl ether acetate.

9. The nail polish remover of claim 8 wherein the ether comprises propylene glycol monomethyl ether, ethylene glycol monopropyl ether, or ethylene glycol monobutyl ether.

10. A nail polish remover consisting essentially of: (a) about 25 to 95% glycol ether ester; (b) about 5 to 75% glycol ether; (c) about 5 to 40% water; (d) an effective amount up to about 15% co-solvent; and (e) an effective amount up to about 5% aesthetic agent.

11. The nail polish remover of claim 10 wherein the ester comprises propylene glycol monomethyl ether acetate.

12. The nail polish remover of claim 10 wherein the ether comprises propylene glycol monomethyl ether.

13. The nail polish remover of claim 12 wherein the co-solvent comprises 2-methyl-1,3-propanediol, propylene glycol, or polyoxypropylene-polyoxyethylene block copolymer.

14. The nail polish remover of claim 13 wherein the aesthetic agent comprises fragrances, colorings, or emollients.

\* \* \* \* \*